United States Patent
Hunt et al.

[19]

[11] Patent Number: 6,142,982
[45] Date of Patent: Nov. 7, 2000

[54] PORTABLE WOUND TREATMENT APPARATUS

[75] Inventors: Kenneth William Hunt, Wimborne; Keith Patrick Heaton, Poole, both of United Kingdom

[73] Assignee: KCI Medical Limited, Oxfordshire, United Kingdom

[21] Appl. No.: 09/078,223

[22] Filed: May 13, 1998

Related U.S. Application Data

[63] Continuation of application No. PCT/GB96/02802, Nov. 14, 1996.

[30] Foreign Application Priority Data

Nov. 14, 1995 [GB] United Kingdom ................... 9523253
Nov. 14, 1996 [WO] WIPO ..................... PCT/GB96/02802

[51] Int. Cl.$^7$ ....................................................... A61M 1/00
[52] U.S. Cl. .......................................... 604/313; 604/317
[58] Field of Search ................................. 604/66, 67, 35, 604/118, 119, 289, 290, 304, 305, 308, 313, 315, 317, 319, 322, 327; 600/573, 578, 29–32; 417/410

[56] References Cited

U.S. PATENT DOCUMENTS

| | | |
|---|---|---|
| 3,026,874 | 3/1962 | Stevens . |
| 3,066,672 | 12/1962 | Crosby et al. ........................ 128/276 |
| 3,089,492 | 5/1963 | Owens . |
| 3,142,298 | 7/1964 | Koski et al. . |
| 4,261,360 | 4/1981 | Perez ....................................... 128/230 |
| 4,444,545 | 4/1984 | Sanders et al. ............................. 417/8 |
| 4,468,219 | 8/1984 | George et al. ............................. 604/66 |
| 4,710,165 | 12/1987 | McNeil et al. ............................. 604/67 |
| 4,930,997 | 6/1990 | Bennett ................................... 604/319 |
| 5,134,994 | 8/1992 | Say ..................................... 128/200.24 |
| 5,449,347 | 9/1995 | Preen et al. .............................. 604/118 |
| 5,678,564 | 10/1997 | Lawrence et al. ....................... 128/761 |
| 5,776,119 | 7/1998 | Bilbo et al. ............................. 604/317 |
| 5,827,246 | 10/1998 | Bowen ................................... 604/313 |

FOREIGN PATENT DOCUMENTS

| | | |
|---|---|---|
| 43 06 478 A1 | 9/1994 | Germany . |
| 295 04 378 U1 | 10/1995 | Germany . |
| 2 220 357 | 1/1990 | United Kingdom . |
| 2 235 877 | 3/1991 | United Kingdom . |
| WO 80/02182 | 10/1980 | WIPO . |
| WO 94/20041 | 9/1994 | WIPO . |

OTHER PUBLICATIONS

International Search Report, PCT/GB96/02802, Apr. 1997.

*Primary Examiner*—John G. Weiss
*Assistant Examiner*—David J. Cho
*Attorney, Agent, or Firm*—Wayne J. Colton, Inc.

[57] ABSTRACT

A portable wound treatment apparatus, for stimulating the healing of superficial wounds, comprises a housing containing a suction pump and a canister for containing fluids drawn from the wound. The housing is supported on a harness or belt worn by the patient. The canister is connected to a porous wound dressing at the wound site via a plurality of tubes, a multi-lumen tube or a combination thereof. A rechargeable battery pack may be incorporated within the housing or provided externally thereto. In the case of an external battery pack, the pack may be shaped to balance the housing on the harness or belt. In operation, pressure transducers are provided to monitor and, if desired, report pressures at the wound site or internal to the canister. Monitored pressures may also be utilized to determine the filled state of the canister and, thereafter, either report this state to the operator or automatically discontinue suction from the wound, or both.

19 Claims, 5 Drawing Sheets

PORTABLE WOUND TREATMENT APPARATUS

RELATED APPLICATIONS

This application is a continuation of PCT international application Ser. No. PCT/GB96/02802 filed Nov. 14, 1996, which designates the United Stites and claims priority to British patent application No. 9523253.4 filed Nov. 14, 1995.

FIELD OF THE INVENTION

The present invention relates to the healing of wounds. More particularly, the invention relates to an apparatus for stimulating the healing of superficial wounds.

BACKGROUND OF THE INVENTION

PCT Application No. GB95/01983 (WO 96/05873) describes apparatus for stimulating the healing of wounds comprising a porous pad which is permeable to fluids for introduction into the wound, a dressing for covering the wound and providing an air-tight seal around the wound, a drainage tube connecting the pad to a suction pump so that negative pressure can be applied to the wound to draw fluids therefrom and a canister for collecting fluids sucked from the wound. The apparatus described in the above application has proven to be clinically effective but there are some limitations in its use.

The apparatus described in the above PCT application is effective for treating a wide variety of different types and sizes of wounds. However, it may require the patient to undergo treatment on the apparatus for a long period. In cases where the patient is confined to bed this may not be a major problem, but where the patient is mobile it means that he or she would be confined for long periods while the treatment takes place.

An object of this invention is therefore to provide apparatus which can be used more conveniently, especially by patients who are reasonably mobile, and which has certain further advantages which will become apparent from the following description.

SUMMARY OF THE INVENTION

In accordance with the foregoing object, there is provided in one aspect of the present invention a portable therapeutic apparatus for stimulating the healing of superficial wounds in a person, which comprises a housing containing a suction pump and a canister for containing fluids drawn from the wound by said pump, said canister including means for connection to a dressing in the region of the wound and a harness or belt for supporting the housing on the person.

Typically, the housing will have a curved surface on the side intended to be supported against the person's body so as to make the apparatus more comfortable to wear. In addition, controls and indicators indicating the status of the treatment being applied to the wound are preferably located on the upper side of the housing so that the patient can easily see, e.g., the level of suction pressure being applied and the program for such treatment.

The suction pump is conveniently driven by an electric motor and batteries for such motor may be contained within the housing. However, it is generally more convenient to provide a separate housing for the batteries since these can be placed on the belt or harness in such a way as to balance the weight of the housing, preferably in a housing shaped similarly to the housing for the pump and canister. The canister should be removably mounted within the housing, e.g. by means of a latch or release mechanism, so that the canister can be readily removed and replaced when full.

In a portable therapeutic apparatus (in contrast with a static apparatus of the kind described in the above PCT application which cannot be easily carried by the patient), it is less easy to determine the pressure prevailing at the wound site being treated. This is because the pressure will depend, in part, upon the hydrostatic height between the pump and the wound being treated and this height may vary during the treatment, depending upon the patient's movements. The apparatus in accordance with the invention overcomes this problem by providing an additional conduit connecting the wound site or an area close thereto to a pressure-detecting means, preferably located in the housing. The pressure-detecting means can be linked to a microprocessor programmed to maintain such pressure within a predetermined range irrespective of the movement of the patient. This can be done by, for example, signaling the pump to increase its speed where the hydrostatic pressure increases between the pump and the wound site or, conversely, reducing its speed where the hydrostatic pressure is reduced. This feature can also be used in a static therapeutic apparatus of the kind described in the above-mentioned PCT application.

In the apparatus described in the above PCT application, the level of liquid in the canister is monitored by capacitance measurement. It has now been found that a simpler way of determining when the canister is filled is by measuring or detecting the pressure drop across the canister. The pressure drop can be increased by providing a filter barrier in the region of the outlet end of the canister. Thus, when the liquid reaches a level within the canister so as to substantially occlude the filter, a sharp pressure change occurs in the conduit between the canister and the pump. By monitoring this pressure change, the point at which the canister is filled can be accurately determined.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 2A:
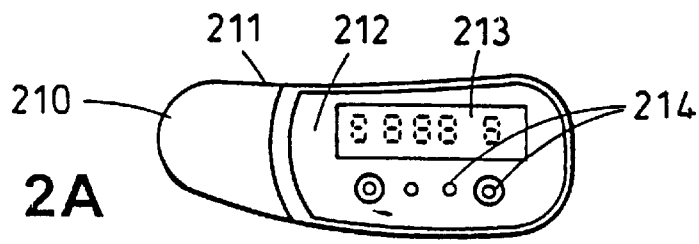
FIGS. 2A and 2B are pictorial representations of the housing of the pump and canister.
Figure 2B:
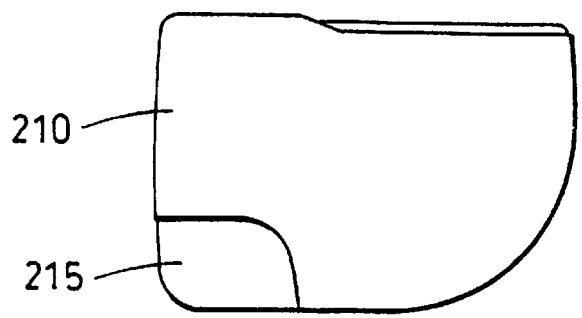

Referring to the drawings, the portable therapeutic apparatus comprises a housing 210 (best shown in FIGS. 2A and 2B), having rounded corners and a side 211 which is concavely curved in order to fit comfortably to the wearer's body. The shaping of the housing with curved surfaces is to avoid sharp corners or edges that could dig in to the user or his caregiver. The upper surface 212 is generally flat and has an LCD screen 213 on which details such as applied pressure can be displayed. Control buttons 214 are provided to adjust pressures and treatment intervals. Provision is made for housing a canister within the housing and a snap release cover 215 is arranged for removing or introducing the canister.

Figure 3A:
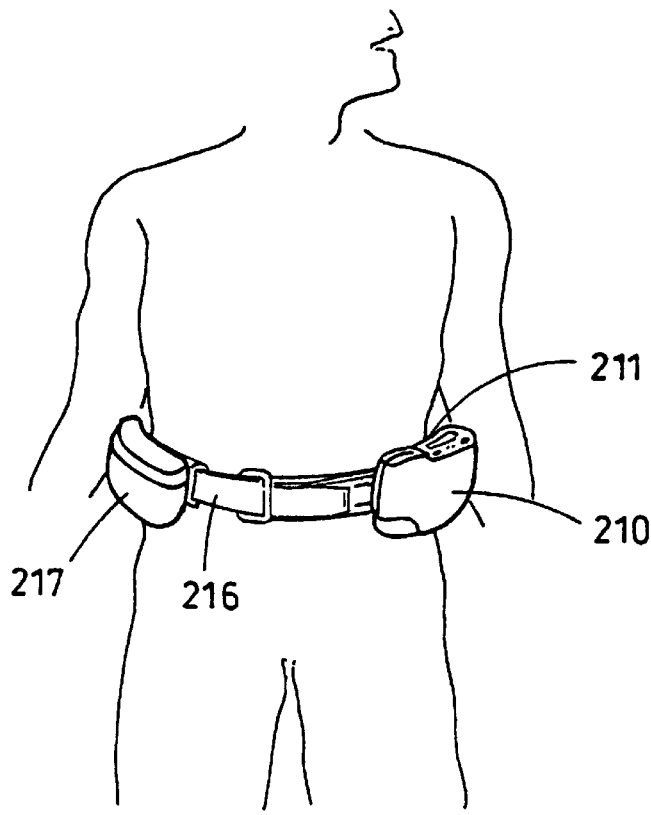
FIGS. 3A and 3B are pictorial representations of the apparatus supported on a belt and harness respectively.
Figure 3B:
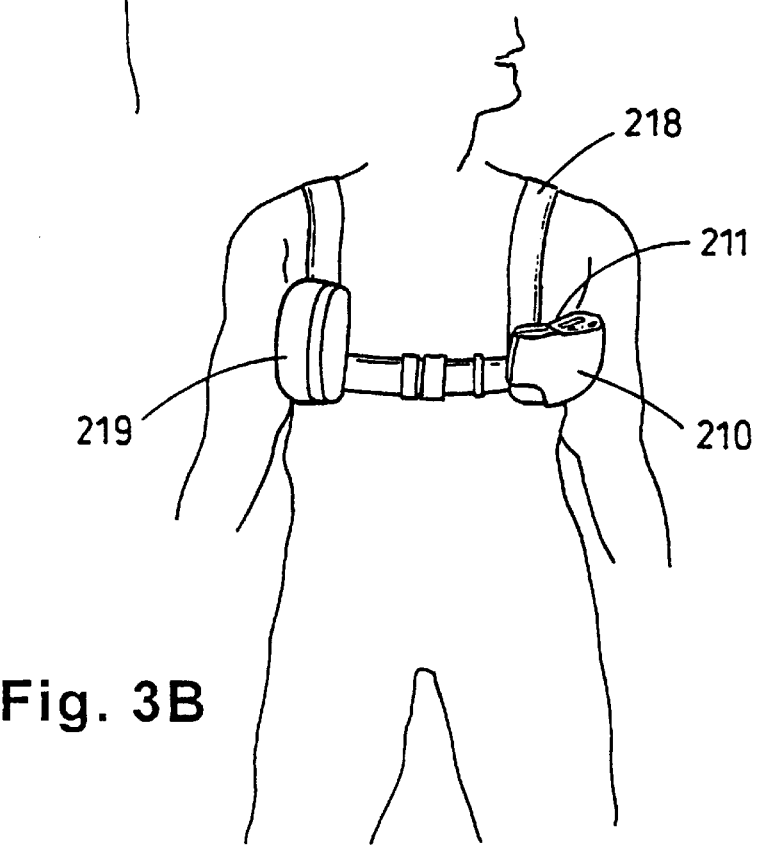

FIGS. 3A and 3B show schematically ways in which the housing 210 may be supported on the patient's body. In FIG. 3A the housing 210 is supported on a belt 216 and its weight is balanced by a similarly rounded casing 217 containing a rechargeable battery pack. FIG. 3B shows an alternative arrangement in which the housing is supported on a harness 218 and again a battery pack is contained in a housing 219, also supported on the harness.

Figure 4:
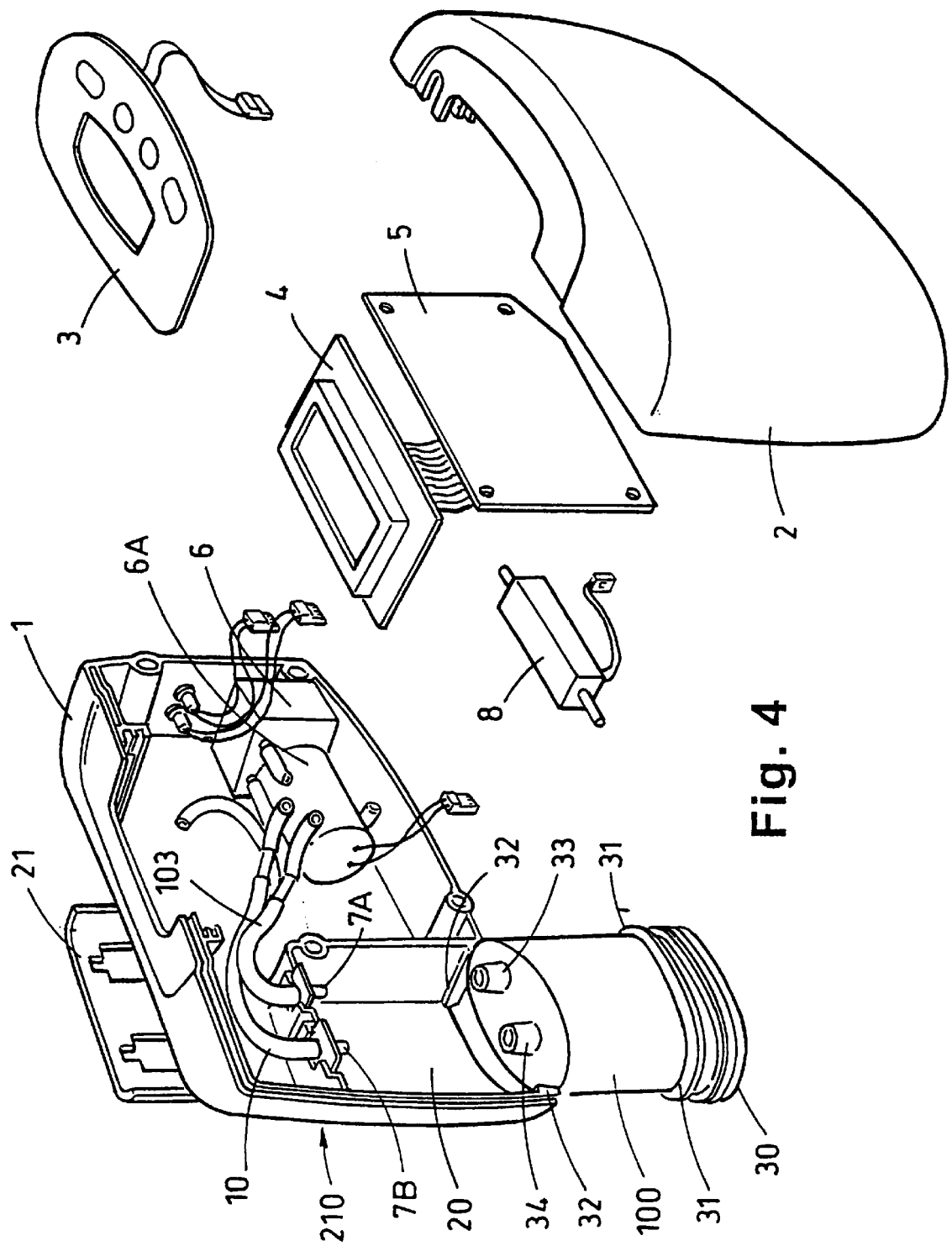
FIG. 4 is an exploded view of the housing showing the contents.

FIG. 4 shows an exploded view of the housing 210 indicating the main components within the housing. The housing consists of front and rear shell moldings 1 and 2 having an external belt clip 21 for attachment to a belt or harness.

Within housing shell 1 is located a suction pump 6 with associated electric motor 6A and the pump is connected by a silicon rubber tube 103 to a canister spigot 7A in a compartment 20 for the canister 100. Also connected to a second canister spigot 7B via a tube 10 is a pressure relief valve 8 and both tubes 103 and 10 are connected via T-connectors T to pressure transducers (not shown). A microprocessor 4 is mounted on a PCB board 5 and a membrane assembly 3 incorporates an LCD indicator and control buttons.

The apparatus may include means for recording pressures and treatment conditions given to a particular patient which may be printed out subsequently by the physician. Alternatively, the equipment may include a modem and a telephone jack so that the conditions under which the patient has been treated can be interrogated by the physician from a distant station.

Canister 100 is a push fit into the cavity 20 and its lower end is supported in a cover 30. The cover 30 incorporates fingers 31 which are releasably engageable with lips 32 to hold the canister in position. The canister and the latch mechanism is arranged so that when the latch is engaged, the spigots 7A and 7B are in sealing engagement or abutment with tubular protrusions 33 and 34 formed in the top of the canister.

Figure 1:
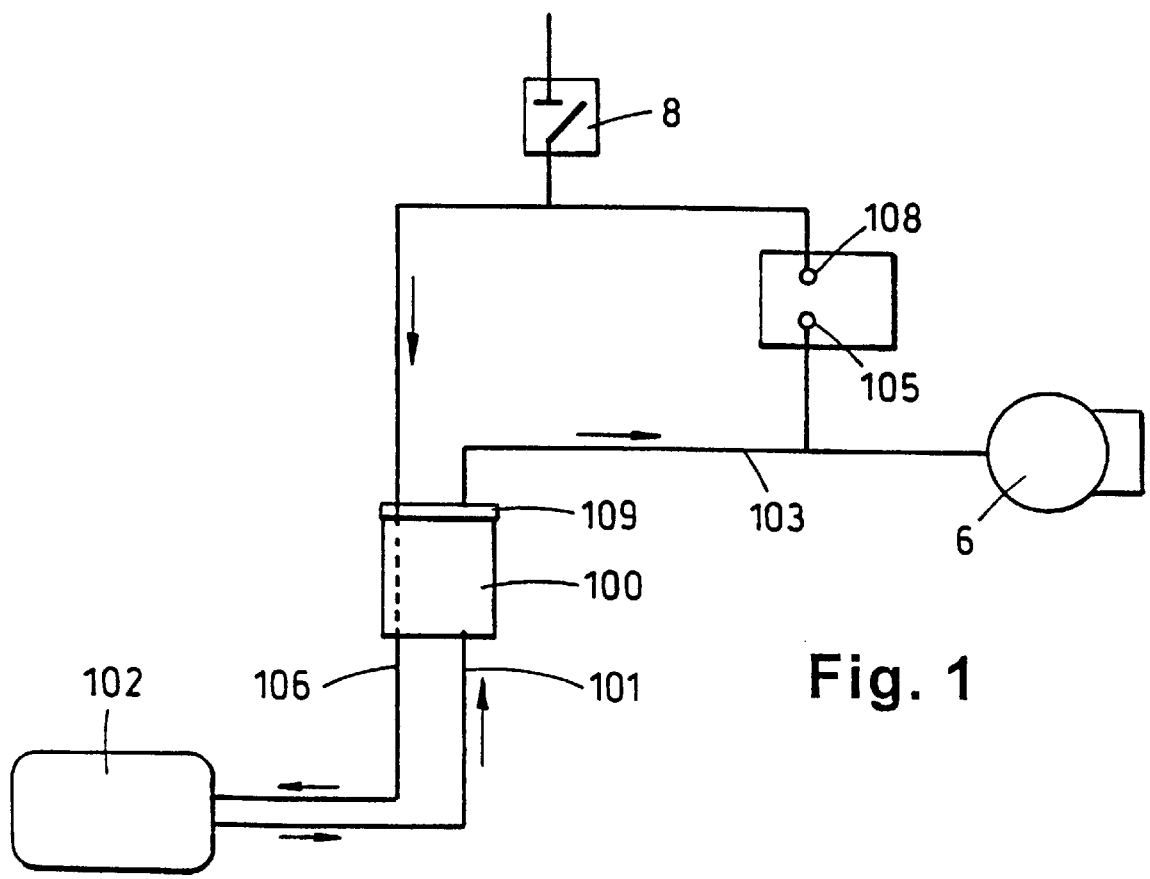
FIG. 1 is a schematic layout of the apparatus in accordance with the invention.

The method of operation of the apparatus can be appreciated from the schematic layout in FIG. 1, in which the canister 100 is connected via tube 101 to a porous dressing 102 at the wound site. Suction is applied to the wound site via the canister by a tube 103, connected to the pump 6. The pressure in the tube 103 is detected by the transducer 105.

A second tube 106 is connected to the wound site 102 at one end, and also to a pressure relief valve 8 and to a second transducer 108. Tubes 106 and 101 can be combined in a multi-partitioned tube in manner to be described later. By means of tube 106 and transducer 108 the pressure at the wound site can be measured or monitored. A filter 109 is placed at or close to the outlet end of the canister 100 to prevent liquid or solid particles from entering the tube 103. The filter is a bacterial filter which is hydrophobic and preferably also lipophobic. Thus, aqueous and oily liquids will bead on the surface of the filter. During normal use there is sufficient air flow through the filter such that the pressure drop across the filter is not substantial.

As soon as the liquid in the canister reaches a level where the filter is occluded, a much increased negative pressure occurs in tube 103 and this is detected by transducer 105. Transducer 105 is connected to circuitry which interprets such a pressure change as a filled canister and signals this by means of a message on the LCD and/or buzzer that the canister requires replacement. It may also automatically shut off the working of the pump.

In the event that it is desired to apply intermittent suction to the wound site, a pressure relief valve 8 enables the pressure at the wound site to be brought to atmospheric pressure rapidly. Thus, if the apparatus is programmed, for example, to relieve pressure at 10 minute intervals, at these intervals valve 8 will open for a specified period, allow the pressure to equalize at the wound site and then close to restore the suction. It will be appreciated that when constant suction (or negative pressure) is being applied to the wound site, valve 8 remains closed and there is no leakage from atmosphere. In this state, it is possible to maintain negative pressure at the wound site without running the pump continuously, but only from time to time, to maintain a desired level of negative pressure (i.e. a desired pressure below atmospheric), which is detected by the transducer 105. This saves power and enables the appliance to operate for long periods on its battery power supply.

Instead of running two separate tubes to the wound site, it is preferable to contain tubes 106 and 101 in a single tube which is connected through the canister. Thus, for example, tubes 103 and 101 may comprise an internal tube surrounded by an annular space represented by tube 106. This is illustrated in FIGS. 5A to 5F and in a modified form in FIG. 6E.

Figure 6A:
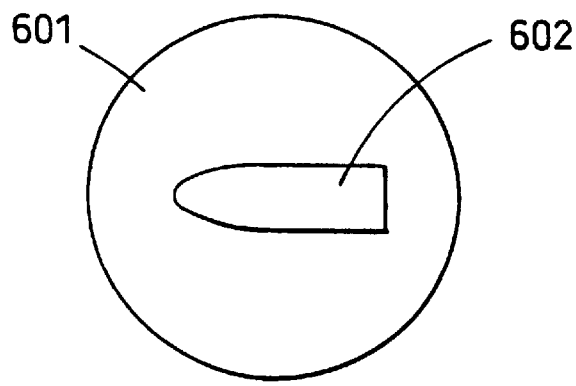
FIGS. 6A to 6D show various views of a foam dressing connector for connecting the housing to the dressing.
Figure 6B:
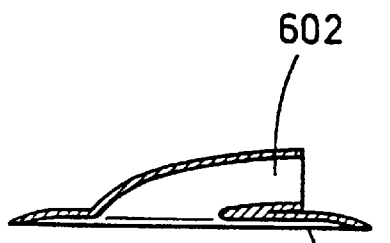
Figure 6C:
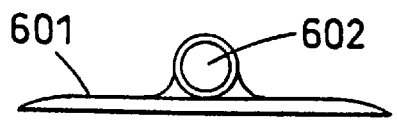
Figure 6D:
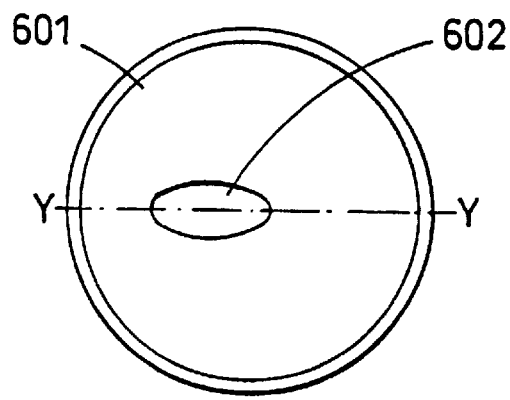
Figure 6E:
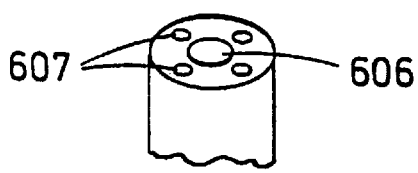
FIG. 6E shows a section of a modified multi-lumen tube.

In an alternative embodiment, the multi-lumen tube may be constructed as shown in FIG. 6E. In this embodiment, the internal bore 606 comprises the line 101 (see FIG. 1) and is used to extract fluids from the wound site. Air flow (represented by line 106 in FIG. 1) passes down conduits 607 located within the walls of the tube. By spacing the conduits 607 at 90° intervals around the tube, the risk of arresting the air flow by kinking or twisting the multi-lumen tube is minimized.

Figure 5A:
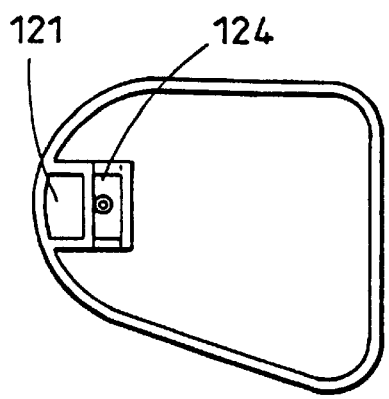
FIGS. 5A to 5F show various views of a preferred form of the canister and a section of a multi-lumen tube.
Figure 5D:
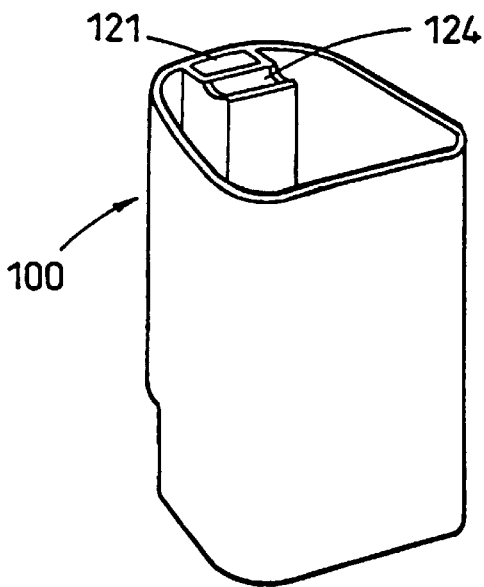
Figure 5B:
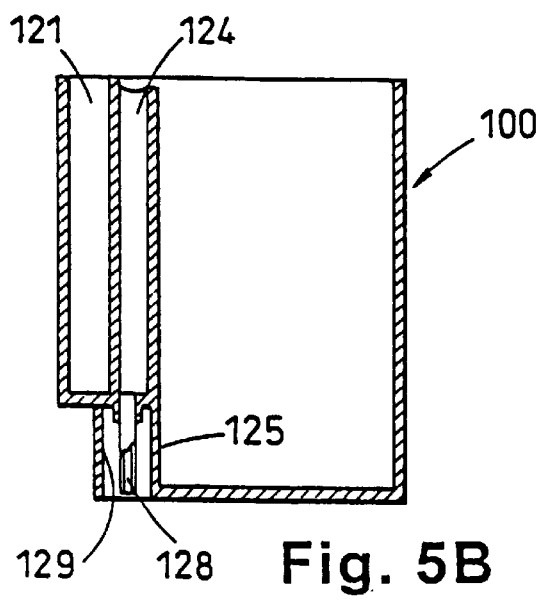
Figure 5E:
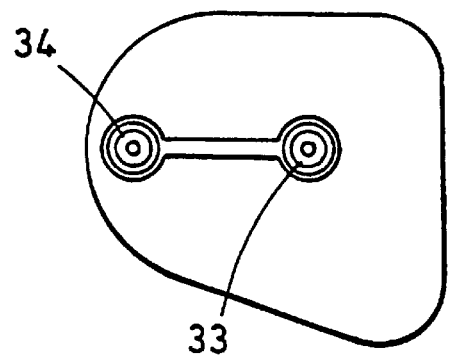
Figure 5C:
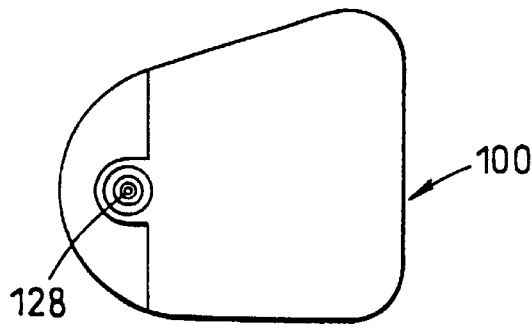
Figure 5F:
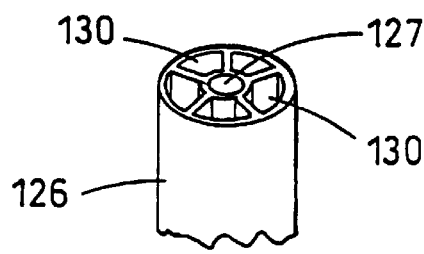

FIG. 5E is a plan view of the top of a preferred shape of the canister, the generally triangular shape in section being chosen to fit better the space within cavity 20 (see FIG. 4). Tubular protrusions on the top of the canister are connected internally of the canister with respectively conduits 124 and 121 (see sectional view of FIG. 5B), thus maintaining a separation between the tubes which are represented by lines 103 and 106 in FIG. 1. At the base of the canister, a molding 125 facilitates connection to a multi-partitioned tube 126 shown in FIG. 5F. Tube 126 has a central bore 127 that is sized to fit over a spigot 128 in molding 125. At the same time, the external wall of tube 126 seals against the inner wall 129 of molding 125. Thus, compartment 124 will connect with central bore 127 and the compartment 121 will connect with the annular spaces 130 of tube 126. In this way, a conduit 130 corresponds with line 106 and central bore 127 with line 101 as shown in FIG. 1.

The partitioned tube need not continue all the way to the wound site 102, but can be connected to a short section of single bore tube close to the wound site.

In the event of an air leak in the dressing at the wound site 102, this can be detected by both transducers 105 and 108 reading insufficient negative pressure for a specific time period, and then triggering a leak alarm, i.e. a message on the LCD, preferably also with an audible warning.

Typically, the pump 6 is a diaphragm pump but other types of pump and equivalent components to those specifically employed may be substituted.

Figure 7A:
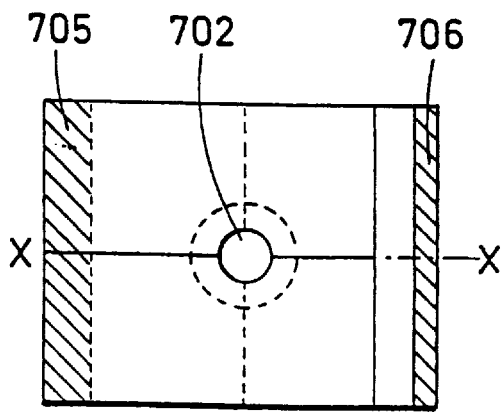
FIGS. 7A and 7B show a plan and perspective view of a surgical drape for use with the apparatus.
Figure 7B:
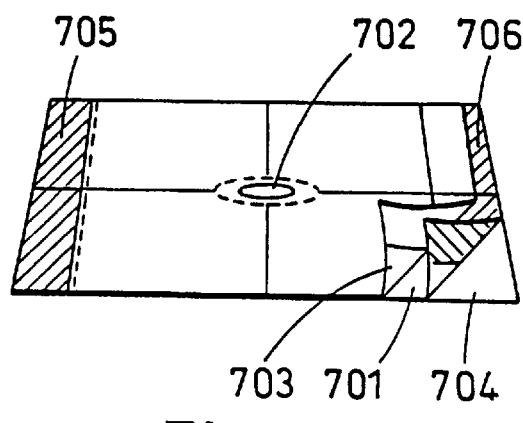

FIGS. 6A–6D show various views of a connector for attaching the multi-lumen tube at the wound site. FIGS. 7A and 7B show a plan and perspective view of a surgical drape for attaching the connector to a porous dressing at the wound site. The connector comprises a molded plastics disc-like cup 601 having a centrally positioned spout 602. The spout 602 is sized to accept, as a closely sliding fit, the end of a multi-lumen tube, e.g. of the kind shown in FIGS. 5F or 6E. In use, a porous dressing is cut to correspond with the extent of the wound and pressed onto the wound as shown in FIG. 10 of our above-cited PCT application WO 96/05873. Instead of introducing the lumen into the foam dressing, the cup 601 is pressed onto the porous dressing and secured by a surgical drape. However, if desired, the end of the lumen can be passed into the spout and additionally pressed into the foam. A surgical drape, such as shown in FIGS. 7A and 7B, can be used to secure the connector, lumen and dressing. The drape comprises a polyurethane film 701 coated on one side with a pressure-sensitive acrylic resin adhesive. A hole 702 is cut through all layers of the drape and the hole is dimensioned to correspond approximately with the outer cross-section of the spout 602. Film 701 has an overall size that allows it to be adhered to the patient's skin around the wound site while, at the same time, securing the connector to the porous dressing. A sufficient overlap around the wound is provided so that an airtight cavity is formed around the wound.

In an alternative form, the drape can be made in two parts, e.g. by cutting along the line X—X in FIG. 7A. With this arrangement, the wound can be sealed by overlapping two pieces of surgical drape so that they overlap each other along a line Y—Y as shown in FIG. 6D.

The surgical drape may include a protective film 703, e.g. of polyethylene, and a liner 704 that is stripped off prior to use to expose the pressure-sensitive adhesive layer. The polyurethane film may also include handling bars 705, 706, which are not coated with adhesive, to facilitate stretching of the film over the wound site. The dressing is preferably a pad of porous, flexible plastics foam, e.g. reticulated, open intercommunicating cellular flexible polyurethane foam, especially of the kind described in the above-mentioned PCT application WO 96/05873.

Alternatively, a reticulated intercommunicating cellular foam made from flexible polyvinylacetate or polyvinylalcohol foam may be used. The latter is advantageous because it is hydrophilic. Other hydrophilic open celled foams may be used.

In another method of therapy, the foam dressing may be sutured into a wound after surgery and the foam dressing connected to the pump unit by the multi-lumen catheter. Negative pressure can then be applied continuously or intermittently for a period determined by the surgeon, e.g. from about 6 hours to 4 to 5 days. After this period, the dressing is removed and the wound re-sutured. This therapy improves the rate of granulation and healing of wounds after surgery.

While the foregoing description is exemplary of the preferred embodiments of the present invention, those of ordinary skill in the relevant arts will recognize the many variations, alterations, modifications, substitutions and the like as are readily possible, especially in light of this description, the accompanying drawings and claims drawn thereto. In any case, because the scope of the present invention is much broader than any particular embodiment, the foregoing detailed description should not be construed as a limitation of the scope of the present invention, which is limited only by the claims appended hereto.

What is claimed is:

1. A therapeutic apparatus for stimulating the healing of a wound in a mammal, said apparatus comprising:

a porous pad for introduction into the wound, said porous pad being permeable to liquids;

a dressing for covering the wound site, said dressing providing a substantially air-tight seal around the wound;

a suction pump in fluid communication with said porous pad through a drainage conduit and a canister, said canister being interposed between said drainage conduit and said suction pump such that said suction pump is adapted to draw, through said drainage conduit and into said canister, liquid from said sealed porous pad;

a filter interposed between said suction pump and said canister for preventing liquid collected in said canister from being introduced into said suction pump; and a pressure detection conduit for providing fluid communication between said porous pad and a first pressure detector, whereby pressure at the wound may be substantially directly monitored.

2. The therapeutic apparatus as recited in claim 1, said apparatus further comprising a relief valve in fluid communication with said pressure detection conduit, said relief valve being adapted to admit air into said pressure detection conduit thereby relieving suction therein.

3. The therapeutic apparatus as recited in claim 2, said apparatus further comprising a controller adapted to operate said relief valve such that suction at the wound may be intermittently applied and relieved.

4. A therapeutic apparatus for stimulating the healing of a wound in a mammal, said therapeutic apparatus comprising:

a porous pad for introduction into the wound, said porous pad being permeable to liquids;

a dressing for covering the wound site, said dressing providing a substantially air-tight seal around the wound, a suction pump in fluid communication with said porous pad through a drainage conduit and a canister, said canister being interposed between said drainage conduit and said suction pump such that said suction pump is adapted to draw, through said drainage conduit and into said canister, liquid from said sealed porous pad;

a filter interposed between said suction pump and said canister for preventing liquid collected in said canister from being introduced into said suction pump;

an outlet conduit fluidly connected between an outlet port of said canister and said suction pump, said filter being disposed in said canister substantially at the interface between said outlet port and said outlet conduit; and a first pressure detector in fluid communication with said outlet conduit, said first pressure detector being adapted to detect pressure changes in said outlet conduit indicative of said canister being filled with liquid.

5. The therapeutic apparatus as recited in claim 4, wherein said first pressure detector is adapted to detect a pressure drop indicative of said filter being substantially covered with liquid.

6. The therapeutic apparatus as recited in claim 5, wherein said filter is hydrophobic.

7. The therapeutic apparatus as recited in claim 5, wherein said filter is lipophobic.

8. The therapeutic apparatus as recited in claim 5, wherein said filter is adapted to cover the entire outlet port of said canister and wherein said filter further comprises tiny pores, said pores being sufficiently small to cause a sharp decrease in pressure in said outlet conduit when said filter is substantially coated with liquid.

9. The therapeutic apparatus as recited in claim 4, wherein:

said therapeutic apparatus further comprises a pressure detection conduit for providing fluid communication between said porous pad and a second pressure detector, whereby pressure at the wound site may be substantially directly monitored; and said drainage conduit and said pressure detection conduit are formed together in a unitary communication line.

10. The therapeutic apparatus as recited in claim 9, wherein said unitary communication line comprises a tube, said tube being longitudinally partitioned to provide said drainage conduit through which suction is applied to the wound and said pressure detection conduit through which pressure at the wound may be detected.

11. The therapeutic apparatus as recited in claim 10, comprising a plurality of pressure detection conduits, said pressure detection conduits being arranged circumferentially about said drainage conduit.

12. The therapeutic apparatus as recited in claim 10, comprising a plurality of drainage conduits, said drainage conduits being arranged circumferentially about said pressure detection conduit.

13. The therapeutic apparatus as recited in claim 4, wherein said suction pump and said canister are contained in a housing, said housing being adapted to be worn on a belt.

14. The therapeutic apparatus as recited in claim 13, wherein said housing comprises a curved side, said curved side being adapted to fit snugly adjacent a wearer's body.

15. The therapeutic apparatus as recited in claim 14, said apparatus further comprising controls in operable communication with said suction pump, said controls being disposed on an upper side of said housing for easy access thereto by the wearer.

16. A therapeutic apparatus for stimulating the healing of a wound in a mammal, said apparatus comprising:

a porous pad for introduction into the wound, said porous pad comprising a polyvinyl alcohol foam having an intercommunicating cellular structure permeable to liquids;

a dressing for covering the wound site, said dressing comprising a film having a pressure-sensitive adhesive coating thereon, said coating being adapted to provide a substantially air-tight seal around the wound;

a negative pressure source in fluid communication with said porous pad through a drainage conduit, said drainage conduit being adapted to pass through said dressing; and said film being adapted to maintain said substantially air-tight seal and said negative pressure source being adapted to draw a flow of liquid from said porous pad into said drainage conduit while said drainage conduit is positioned through said dressing.

17. The therapeutic apparatus as recited in claim 16, wherein said film comprises polyurethane.

18. The therapeutic apparatus as recited in claim 16, said apparatus further comprising:

an aperture through said film; and a connector for providing fluid communication between said porous pad and said drainage conduit, said connector being adapted to pass through said aperture.

19. The therapeutic apparatus as recited in claim 18, said connector further comprising:

a flange for sealing said connector to said dressing through contact with said pressure-sensitive adhesive coating; and a spout adapted to pass through said aperture and attach to said drainage conduit.

* * * * *